United States Patent [19]
Ebel

[11] Patent Number: 5,179,210
[45] Date of Patent: Jan. 12, 1993

[54] PREPARATION OF N-SUBSTITUTED IMIDAZOLES

[75] Inventor: Kraus Ebel, Mutterstadt, Fed. Rep. of Germany

[73] Assignee: BASF Aktiengesellschaft, Ludwigshafen, Fed. Rep. of Germany

[21] Appl. No.: 695,980

[22] Filed: May 6, 1991

[30] Foreign Application Priority Data

May 15, 1990 [DE] Fed. Rep. of Germany ....... 4015535

[51] Int. Cl.⁵ ................ C07D 233/68; C07D 233/54; C07D 235/02; C07D 235/04
[52] U.S. Cl. .......................... 548/335.1; 548/343.5; 548/346.1; 548/341.1; 548/345.1; 548/342.5; 548/343.1; 548/304.4; 548/310.7; 548/310.1; 548/302.7
[58] Field of Search ............... 548/337, 341, 342, 346, 548/329, 330, 333, 334, 325, 323, 335

[56] References Cited

FOREIGN PATENT DOCUMENTS 2422706 3/1976 Fed. Rep. of Germany .

OTHER PUBLICATIONS

Pilarski, B., *Leibigs Ann. Chem.*, (1983) 1078-1080.

*Primary Examiner*—Floyd D. Higel
*Assistant Examiner*—Lenora Ava Miltenberger
*Attorney, Agent, or Firm*—John H. Shurtleff

[57] ABSTRACT

A process for preparing N-substituted imidazoles of the formula I

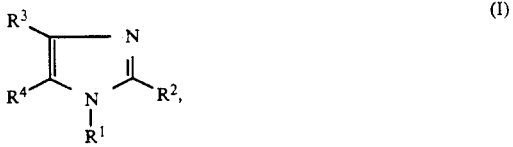

where
$R^1$ is $C_1$-$C_{20}$-alkyl, $C_2$-$C_{20}$-alkenyl, $C_2$-$C_{20}$-alkynyl, $C_2$-$C_{20}$-alkoxyalkyl, $C_3$-$C_{20}$-alkenyloxyalkyl, $C_3$-$C_{12}$-cycloalkyl, $C_4$-$C_{20}$-cycloalkylalkyl, or $C_7$-$C_{20}$-arylalkyl or aryl which is unsubstituted or substituted by $C_1$-$C_8$-alkyl, $C_1$-$C_8$-alkoxy, halogen, $C_1$-$C_4$-haloalkyl, $C_1$-$C_4$-haloalkoxy or phenoxy,
$R^2$, and $R^4$ are each, independently of one another, hydrogen, $C_1$-$C_{20}$-alkyl, $C_2$-$C_{20}$-alkoxyalkyl, $C_3$-$C_{12}$-cycloalkyl, halogen, $C_7$-$C_{20}$-arylalkyl or aryl which is unsubstituted or substituted by $C_1$-$C_8$-alkyl, $C_1$-$C_8$-alkoxy, halogen, $C_1$-$C_4$-haloalkyl, $C_1$-$C_4$-haloalkoxy or phenoxy, or $R^3$ and $R^4$ together form $(CH_2)_n$ or $(CH=CH)_m$ which is unsubstituted or mono- or disubstituted by $C_1$-$C_8$-alkyl, $C_1$-$C_8$-alkoxy and/or halogen and in which n is from 1 to 6 and m is from 1 to 3, by reacting imidazoles of the formula II

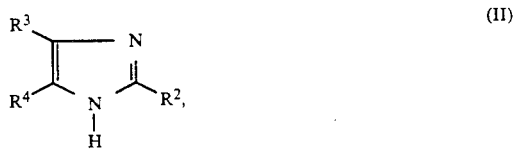

where $R^2$, $R^3$ and $R^4$ have the abovementioned meanings, with halides of the formula III

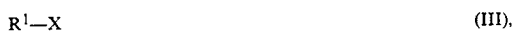

where X is chlorine, bromine or iodine, and $R^1$ has the abovementioned meanings, in aqueous hydroxide solutions at from 0° to 100° C., wherein the reaction is carried out from the beginning of the reaction in the presence of from 0.1 to 50 mol % of any N-substituted imidazole as a catalyst based on the imidazole reactant II.

9 Claims, No Drawings

PREPARATION OF N-SUBSTITUTED IMIDAZOLES

The present invention relates to a novel process for preparing N-substituted imidazoles by reacting imidazoles which are unsubstituted on the nitrogen (carry a hydrogen atom) with halides and aqueous hydroxide solutions in the presence of N-substituted imidazoles.

Liebigs Ann. Chem. (1983), 1078–1080 discloses a process for the alkylation of imidazoles to synthesize 1-alkylimidazoles. In this process, imidazole is reacted with methyl iodide or 2-methylimidazole is reacted with ethyl iodide, with 50 % strength sodium hydroxide solution as reagent, directly to 1-methylimidazole or 1-ethyl-2-methylimidazole.

However, this process has disadvantages for use on the industrial scale, such as the reaction being exothermic and not starting until after a latency period and then being difficult to control on the large scale, as well as unsatisfactory yields.

It is an object of the present invention to remedy the abovementioned disadvantages.

We have found that this object is achieved by a novel and improved process for preparing N-substituted imidazoles of the formula I

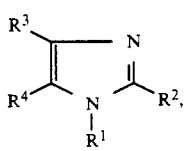

where $R^1$ is $C_1$-$C_{20}$-alkyl, $C_2$-$C_{20}$-alkenyl, $C_2$-$C_{20}$-alkynyl, $C_2$-$C_{20}$-alkoxyalkyl, $C_3$-$C_{20}$-alkenyloxyalkyl, $C_3$-$C_{12}$-cycloalkyl, $C_4$-$C_{20}$-cycloalkylalkyl, or $C_7$-$C_{20}$-arylalkyl or aryl which is unsubstituted or substituted by $C_1$-$C_8$-alkyl, $C_1$-$C_8$-alkoxy, halogen, $C_1$-$C_4$-haloalkyl, $C_1$-$C_4$-haloalkoxy or phenoxy, $R^2$, $R^3$ and $R^4$ are each, independently of one another, hydrogen, $C_1$-$C_{20}$-alkyl, $C_2$-$C_{20}$-alkoxyalkyl, $C_3$-$C_{12}$-cycloalkyl, halogen, $C_7$-$C_{20}$-arylalkyl or aryl which is unsubstituted or substituted by $C_1$-$C_8$-alkyl, $C_1$-$C_8$-alkoxy, halogen, $C_1$-$C_4$-haloalkyl, $C_1$-$C_4$-haloalkoxy or phenoxy, or $R^3$ and $R^4$ together form $(CH_2)_n$ or $(CH=CH)_m$ which is unsubstituted or mono- or disubstituted by $C_1$-$C_8$-alkyl, $C_1$-$C_8$-alkoxy and/or halogen and in which n is from 1 to 6 and m is from 1 to 3, by reacting imidazoles of the formula II

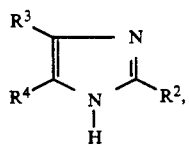

where $R^2$, $R^3$ and $R^4$ have the abovementioned meanings, with halides of the formula III $$R^1-X \quad \text{(III),}$$

where X is chlorine, bromine or iodine, and $R^1$ has the abovementioned meanings, in aqueous hydroxide solutions at from 0° to 100° C., wherein the reaction is carried out from the beginning of the reaction in the presence of from 0.1 to 50 mol % of any N-substituted imidazole as a catalyst and based on the imidazole reactant II.

In principle, any N-substituted imidazole derivatives can be employed as catalysts, preferably those of the formula I. However, it is expedient, for simplicity of working up, to employ as catalyst that N-substituted imidazole derivative I which is to be prepared by the novel process. The amounts of the catalyst are generally from 0.1 to 50 mol % based on imidazole II employed, but are normally from 1 to 20 mol %.

The reaction is normally carried out at from 0° to 100° C., preferably 15° to 75° C., particularly preferably 35° to 60° C. It can also be carried out under superatmospheric pressure to achieve higher temperatures.

Used as reaction medium are aqueous hydroxide solutions, preferably aqueous alkali metal hydroxide solutions such as sodium hydroxide solution, in an amount of more than 1 mole of hydroxide solution per mole of imidazole II employed. The hydroxide solutions generally contain from 10 to 70% by weight hydroxide, preferably to 60% by weight, particularly preferably 50% by weight. It is also possible to add organic solvents without impeding the reaction, although this reduces the space-time yield.

Suitable meanings for $R^1$ to $R^4$ and n and m in the formulae I to III and X in formula III are, independently of one another:

$R^1$ unbranched or branched $C_1$-$C_{20}$-alkyl, preferably unbranched or branched $C_1$-$C_{12}$-alkyl such as methyl, ethyl, n-propyl, iso-propyl, n-butyl, iso-butyl, sec-butyl, tert-butyl, n-pentyl, isopentyl, sec-pentyl, tert-pentyl, neo-pentyl, 1,2-dimethylpropyl, n-hexyl, isohexyl, sec-hexyl, n-heptyl, iso-heptyl, n-octyl, iso-octyl, n-nonyl, iso-nonyl, n-decyl, iso-decyl, n-undecyl, iso-undecyl, n-dodecyl and iso-dodecyl, unbranched or branched $C_2$-$C_{20}$-alkenyl, preferably unbranched or branched $C_2$-$C_8$-alkenyl such as allyl, 2-butenyl, 1-methyl-2-propenyl, 4-butenyl, 2-pentenyl and 2,2-dimethylpentenyl, unbranched or branched $C_2$-$C_{20}$-alkynyl, preferably unbranched or branched $C_2$-$C_8$-alkynyl such as propynyl, 1,1-dimethylpropynyl, 1-methylpropynyl, 1-butynyl, 2-butynyl and 4,4-dibutyl-2-yn-1-yl, unbranched or branched $C_2$-$C_{20}$-alkoxyalkyl, preferably unbranched or branched $C_2$-$C_8$-alkoxyalkyl such as methoxymethyl, ethoxymethyl, n-propoxymethyl, iso-propoxymethyl, n-butoxymethyl, iso-butoxymethyl, sec-butoxymethyl, tert-butoxymethyl, n-pentoxymethyl, iso-pentoxymethyl, sec-pentoxymethyl, tert-pentoxymethyl, neopentoxymethyl, 1,2-dimethylpropoxymethyl, n-hexoxymethyl, iso-hexoxymethyl, sec-hexoxymethyl, n-heptoxymethyl, iso-heptoxymethyl, 1-methoxyethyl, 1-ethoxyethyl, 1-n-propoxyethyl, 1-iso-propoxyethyl, 1-n-butoxyethyl, 1-iso-butoxyethyl, 1-sec-butoxyethyl, 1-tert-butoxyethyl, 1-n-pentoxyethyl, 1-iso-pentoxyethyl, 1-sec-pentoxyethyl, 1-tert-pentoxyethyl, 1-neo-pentoxyethyl, 1-(1,2-dimethylpropoxy)ethyl, 1-n-hexoxyethyl,1-isohexoxylethyl, 1-sec-hexoxyethyl, 2-methoxyethyl, 2-ethoxyethyl, 2-n-propoxyethyl, 2-iso-propoxyethyl, 2-n-butoxyethyl, 2-iso-butoxyethyl, 2-sec-butoxyethyl, 2-tert-butoxyethyl, 2-n-pentoxyethyl, 2-iso-pentoxyethyl, 2-sec-pentoxyethyl, 2-tert-pentoxyethyl, 2-neo-pentoxyethy1,2-(1,2-dimethylpropoxy)ethyl 2-n-hexoxyethyl, 2-isohexoxyethyl and 2-sec-hexoxyethyl, unbranched or branched $C_3$-$C_{20}$-alkenyloxyalkyl, preferably unbranched or branched $C_3$-$C_8$-alkenyloxyalkyl oxyalkyl such as vinyloxymethyl, allyloxymethyl, 1-vinyloxyethyl,1-allyloxyethyl,2-vinyloxyethyl and 2-allyloxyethyl, $C_3$-$C_{12}$-cycloalkyl, preferably $C_3$-$C_8$-cycloalkyl such as cyclopropyl, cyclobutyl, cyclopentyl, cyclohexyl, cycloheptyl and cyclooctyl, $C_4$-$C_{20}$-cycloalkylalkyl, preferably $C_4$-$C_8$-cycloalkylalkyl such as cyclopentylmethyl, 2-cyclopentylethyl, 1-cyclopentylethyl, cyclohexylmethyl, 1-cyclohexylethyl and 2-cyclohexylethyl, aryl, preferably phenyl $C_7$-$C_{20}$-arylalkyl, preferably $C_7$-$C_{12}$-arylalkyl such as benzyl, 1-phenethyl and 2-phenethyl, aryl di- or trisubstituted by $C_1$-$C_8$-alkyl, preferably phenyl di- or trisubstituted by $C_1$-$C_4$-alkyl, such as 2,4-dimethylphenyl, 3,4-dimethylphenyl and 3,4,5-trimethylphenyl, aryl di- or trisubstituted by $C_1$-$C_8$-alkoxy, preferably phenyl di- or trisubstituted by $C_1$-$C_4$-alkoxy, such as 3,4-dimethoxyphenyl and 3,4,5-trimethoxyphenyl, aryl mono- to trisubstituted by $C_1$-$C_4$-haloalkyl, preferably phenyl mono- to trisubstituted by $C_1$-$C_2$-fluoro- and chloroalkyl, particularly preferably phenyl mono- to trisubstituted by trifluoromethyl and trichloromethyl, such as 4-trifluoromethylphenyl and 4-trichloromethylphenyl, aryl mono- to trisubstituted by $C_1$-$C_4$-haloalkoxy, preferably phenyl mono- to trisubstituted by $C_1$-$C_2$-fluoro- and chloroalkoxy, particularly preferably phenyl mono- to trisubstituted by trifluoromethoxy and trichloromethoxy, such as trifluoromethoxyphenyl, aryl mono- to trisubstituted by halogen, preferably phenyl mono- to trisubstituted by fluorine or chlorine, such as 4-chlorophenyl, 3,4-dichlorophenyl, 4-bromophenyl, 4-fluorophenyl and 4-fluoro-3-chlorophenyl, $C_7$-$C_{20}$-arylalkyl mono- to trisubstituted by halogen in the aryl moiety, preferably $C_7$-$C_{10}$-phenylalkyl mono- to trisubstituted by fluorine or chlorine in the phenyl moiety, such as 4-fluorobenzyl, 4-chlorobenzyl, 2,4-dichlorobenzyl and 3,4-dichlorobenzyl, $C_7$-$C_{20}$-arylalkyl mono- to trisubstituted by $C_1$-$C_8$-alkyl in the aryl moiety, preferably $C_7$-$C_{10}$-phenylalkyl mono- to trisubstituted by $C_1$-$C_4$-alkyl in the phenyl moiety, particularly preferably $C_7$-$C_{10}$-phenylalkyl mono- to trisubstituted by $C_1$-$C_2$-alkyl in the phenyl moiety, such as 4-methylbenzyl, 4-ethylphenyl and 4-methylphenethyl, $C_7$-$C_{20}$-arylalkyl mono- to trisubstituted by $C_1$-$C_8$-alkoxy in the aryl moiety, preferably $C_7$-$C_{10}$-phenylalkyl mono- to trisubstituted by $C_1$-$C_4$-alkoxy in the phenyl moiety, particularly preferably $C_7$-$C_{10}$-phenylalkyl mono- to trisubstituted by $C_1$-$C_2$-alkoxy in the phenyl moiety, such as 4-methoxybenzyl, 4-ethoxybenzyl and 4-methoxyphenethyl, $C_7$-$C_{20}$-arylalkyl mono- to trisubstituted by $C_1$-$C_4$-haloalkyl in the aryl moiety, preferably $C_7$-$C_{10}$-phenylalkyl mono- to trisubstituted by $C_1$-$C_2$-fluoro- and chloroalkyl in the phenyl moiety, particularly preferably $C_7$-$C_{10}$-phenylalkyl mono- to trisubstituted by trifluoromethyl and trichloromethyl in the phenyl moiety, such as 4-trifluoromethylbenzyl and 4-trichloromethylbenzyl, $C_7$-$C_{20}$-arylalkyl mono- to trisubstituted by $C_1$-$C_4$-haloalkoxy in the aryl moiety, preferably $C_7$-$C_{10}$-phenylalkyl mono- to trisubstituted by $C_1$-$C_2$-haloalkoxy in the phenyl moiety, particularly preferably $C_7$-$C_{10}$-phenylalkyl mono- to trisubstituted by trifluoromethoxy and trichloromethoxy in the phenyl moiety, such as 4-trifluoromethoxybenzyl and 4-trichloromethoxybenzyl, phenyl substituted by one, two or three phenoxy groups, phenyl di- or trisubstituted by halogen and $C_1$-$C_4$-alkyl, such as 2-methyl-4-chlorophenyl and 3-methyl-4-fluorophenyl, phenyl di- or trisubstituted by halogen and $C_1$-$C_4$-alkoxy, such as 3-chloro-4-methoxyphenyl, phenyl di- or trisubstituted by halogen and $C_1$-$C_4$-haloalkyl, such as 2-chloro-4-trifluoromethylphenyl, phenyl di- or trisubstituted by halogen and phenoxy, such as 3-chloro-4-phenoxyphenyl, phenyl di- or trisubstituted by $C_1$-$C_4$-alkyl and $C_1$-$C_4$-alkoxy, such as 2-methyl-4-methoxyphenyl, phenyl di- or trisubstituted by $C_1$-$C_4$-alkyl and $C_1$-$C_4$-haloalkyl, such as 3-methyl-4-trichloromethylphenyl, phenyl di- or trisubstituted by $C_1$-$C_4$-alkyl and phenoxy, such as 2-methyl-4-phenoxyphenyl, phenyl di- or trisubstituted by $C_1$-$C_4$-alkoxy and $C_1$-$C_4$-haloalkyl, such as 3-trifluoromethyl-4-methoxyphenyl, phenyl di- or trisubstituted by $C_1$-$C_4$-alkoxy and phenoxy, such as 3-methoxy-4-phenoxyphenyl, phenyl di- or trisubstituted by $C_1$-$C_4$-haloalkyl phenoxy, such as 3-trifluoromethyl-4-phenoxyphenyl, phenyl trisubstituted by halogen, $C_1$-$C_4$-alkyl and $C_1$-$C_4$-alkoxy, phenyl trisubstituted by halogen, $C_1$-$C_4$-alkyl and $C_1$-$C_4$-haloalkyl, phenyl trisubstituted by halogen, $C_1$-$C_4$-alkyl and phenoxy, phenyl trisubstituted by halogen, $C_1$-$C_4$-alkoxy and $C_1$-$C_4$-haloalkyl, phenyl trisubstituted by halogen, $C_1$-$C_4$-alkoxy and phenoxy, phenyl trisubstituted by halogen, $c_1$-$C_4$-haloalkyl and phenoxy, phenyl trisubstituted by $C_1$-$C_4$-alkyl, $C_1$-$C_4$-alkoxy and $C_1$-$C_4$-haloalkyl, phenyl trisubstituted by $C_1$-$C_4$-alkyl, $C_1$-$C_4$-alkoxy and phenoxy, phenyl trisubstituted by $C_1$-$C_4$-alkyl, $C_1$-$C_4$-haloalkyl and phenoxy, phenyl trisubstituted by $C_1$-$C_4$-alkoxy, $C_1$-$C_4$-haloalkyl and phenoxy, $R^2$, $R^3$, $R^4$ unbranched or branched $C_1$-$C_{20}$-alkyl, preferably unbranched or branched $C_1$-$C_{12}$-alkyl such as methyl, ethyl, n-propyl, iso-propyl, n-butyl, iso-butyl, sec-butyl, tert-butyl, n-pentyl, iso-pentyl, sec-pentyl, tert-pentyl, neo-pentyl, 1,2-dimethylpropyl, n-hexyl, iso-hexyl, sec-hexyl, n-heptyl, iso-heptyl, n-octyl, iso-octyl, n-nonyl, iso-nonyl, n-decyl, iso-decyl, n-undecyl, iso-undecyl, n-dodecyl and iso-dodecyl, unbranched or branched $C_2$-$C_{20}$-alkoxyalkyl, preferably unbranched or branched $C_2$-$C_8$-alkoxyalkyl such as methoxymethyl, ethoxymethyl, n-propoxymethyl, iso-propoxymethyl, n-butoxymethyl, isobutoxymethyl, sec-butoxymethyl, tert-butoxymethyl, n-pentoxymethyl, iso-pentoxymethyl, sec-pentoxymethyl, tert-pentoxymethyl, neo-pentoxymethyl, 1,2-dimethylpropoxymethyl, n-hexoxymethyl, iso-hexoxymethyl, sec-hexoxymethyl, n-heptoxymethyl, iso-heptoxymethyl, 1-methoxyethyl, 1-ethoxyethyl, 1-n-propoxyethyl, 1-isopropoxyethyl, 1-n-butoxyethyl, 1-iso-butoxyethyl, 1-sec-butoxyethyl, 1-tert-butoxyethyl, 1-n-pentoxyethyl, 1-iso-pentoxyethyl, 1-sec-pentoxyethyl, 1-tert-pentoxyethyl, 1-neo-pentoxyethyl, 1-(1,2-dimethylpropoxy) ethyl, 1-n-hexoxyethyl, 1-isohexoxyethyl, 1-sec-hexoxyethyl, 2-methoxyethyl, 2-ethoxyethyl, 2-n-propoxyethyl, 2-isopropoxyethyl, 2-n-butoxyethyl,2-iso-butoxyethyl, 2-sec-butoxyethyl, 2-tert-butoxyethyl, 2-n-pentoxyethyl, 2-isopentoxyethyl, 2-sec-pentoxyethyl, 2-tert-pentoxyethyl, 2-neo-pentoxyethyl, 2-(1,2-dimethylpropoxy)ethyl,2-n-hexoxyethyl,2isohexoxyethyl and 2-sec-hexoxyethyl, $C_3$-$C_{12}$-cycloalkyl, preferably $C_3$-$C_8$-cycloalkyl such as cyclopropyl, cyclobutyl, cyclopentyl, cyclohexyl, cycloheptyl and cyclooctyl, halogen such as fluorine, chlorine, bromine and iodine, preferably chlorine and bromine, aryl, preferably phenyl, 1-naphthyl, 2-naphthyl, 1-anthryl, 2-anthryl and 9-anthryl, particularly preferably phenyl, $C_7$-$C_{20}$-arylalkyl, preferably $C_7$-$C_{12}$-arylalkyl such as benzyl, 1-phenethyl and 2-phenethyl, $C_7$-$C_{20}$-alkylaryl, preferably $C_7$-$C_{10}$-alkylphenyl such as 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 2-iso-propylphenyl, 3-iso-propylphenyl, 4-iso-propylphenyl, 2-n-butylphenyl, 3-n-butylphenyl, 4-n-butylphenyl, 2-iso-butylphenyl, 3-iso-butylphenyl, 4-iso-butylphenyl, 2-sec-butylphenyl, 3-sec-butylphenyl, 4-sec-butylphenyl, 2-tert-butylphenyl, 3-tert-butylphenyl and 4-tert-butylphenyl, $C_7$-$C_{20}$-alkoxyaryl, preferably $c_7$-$c_{10}$-alkoxyphenyl such as 2-methoxyphenyl, 3-methoxyphenyl, 4-methoxyphenyl,2-ethoxyphenyl,3-ethoxyphenyl, 4-ethoxyphenyl, 2-n-propoxyphenyl, 3-n-propoxyphenyl, 4-n-propoxyphenyl, 2-iso-propoxyphenyl, 3-iso-propoxyphenyl, 4-iso-propoxyphenyl, 2-n-butoxyphenyl, 3-n-butoxyphenyl,4-n-butoxyphenyl, 2-iso-butoxyphenyl, 3-iso-butoxyphenyl, 4-isobutoxyphenyl, 2-sec-butoxyphenyl, 3-sec-butoxyphenyl, 4-sec-butoxyphenyl, 2-tert-butoxyphenyl, 3-tert-butoxyphenyl and 4-tert-butoxyphenyl, aryl di- or trisubstituted by $C_1$-$C_8$-alkyl, preferably phenyl di- or trisubstituted by $C_1$-$C_4$-alkyl, such as 2,4-dimethylphenyl, 3,4-dimethylphenyl and 3,4,5-trimethylphenyl, aryl di- or trisubstituted by $c_1$-$C_8$-alkoxy, preferably phenyl di- or trisubstituted by $C_1$-$C_4$-alkoxy, such as 3,4-dimethoxyphenyl and 3,4,5-trimethoxyphenyl, aryl mono- to trisubstituted by $C_1$-$C_4$-haloalkyl, preferably phenyl mono- to trisubstituted by $C_1$-$C_2$-fluoro- and chloroalkyl, particularly preferably phenyl mono- to trisubstituted by trifluoromethyl and trichloromethyl, such as 4-trifluoromethylphenyl and 4-trichloromethylphenyl, phenyl, aryl mono- to trisubstituted by $C_1$-$C_4$-haloalkoxy, preferably phenyl mono- to trisubstituted by $C_1$-$C_2$-fluoro- and chloroalkoxy, particularly preferably phenyl mono- to trisubstituted by trifluoromethoxy and trichloromethoxy, such as trifluoromethoxyphenyl, aryl mono- to trisubstituted by halogen, preferably phenyl mono- to trisubstituted by fluorine or chlorine, such as 4-chlorophenyl, 3,4-dichlorophenyl, 4-bromophenyl, 4-fluorophenyl and 4-fluoro-3-chlorophenyl, $C_7$-$C_{20}$-arylalkyl, preferably $C_7$-$C_{10}$-phenylalkyl such as benzyl, phenethyl, 1-phenyl-n-propyl, 2-phenyl-n-propyl, 3-phenyl-n-propyl, 1-phenyl-isopropyl, 2-phenyl-iso-propyl, 1-phenyl-n-butyl, 2-phenyl-n-butyl, 3-phenyl-n-butyl, 4-phenyl-n-butyl, 1-phenyl-iso-butyl, 2-phenyl-iso-butyl, 3-phenyl-iso-butyl, 1-phenyl-sec-butyl, 1-benzyl-n-propyl, 2-phenyl-sec-butyl, 3-phenyl-sec-butyl and 1,1-dimethylphenethyl, $C_7$-$C_{20}$-arylalkyl mono- to trisubstitute by halogen in the aryl moiety, preferably $C_7$-$C_{10}$-phenylalkyl mono- to trisubstituted by fluorine or chlorine in the phenyl moiety, such as 4-fluorobenzyl, 4-chlorobenzyl, 2,4-dichlorobenzyl and 3,4-dichlorobenzyl, $C_7$-$C_{20}$-arylalkyl mono- to trisubstituted by $C_1$-$C_8$-alkyl in the aryl moiety, preferably $C_7$-$C_{10}$-phenylalkyl mono- to trisubstituted by $C_1$-$C_4$-alkyl in the phenyl moiety, particularly preferably $C_7$-$C_{10}$-phenylalkyl mono- to trisubstituted by $C_1$-$C_2$-alkyl in the phenyl moiety, such as 4-methylphenyl, 4-ethylphenyl and 4-methylphenethyl, $C_7$-$C_{20}$-arylalkyl mono- to trisubstituted by $C_1$-$C_8$-alkoxy in the aryl moiety, preferably $C_7$-$C_{10}$-phenylalkyl mono- to trisubstituted by $C_1$-$C_4$-alkoxy in the phenyl moiety, particularly preferably $C_7$-$C_{10}$-phenylalkyl mono- to trisubstituted by $C_1$-$C_2$-alkoxy in the phenyl moiety, such as 4-methoxybenzyl, 4-ethoxybenzyl and 4-methoxyphenethyl, $C_7$-$C_{20}$-arylalkyl mono- to trisubstituted by $C_1$-$C_4$-haloalkyl in the aryl moiety, preferably $C_7$-$C_{10}$-phenylalkyl mono- to trisubstituted by $C_1$-$C_2$-fluoro- and chloroalkyl in the phenyl moiety, particularly preferably $c_7$-$C_{10}$-phenylalkyl mono- to trisubstituted by trifluoromethyl and trichloromethyl in the phenyl moiety, such as 4-trifluoromethylbenzyl and 4-trichloromethylbenzyl, $C_7$-$C_{20}$-arylalkyl mono- to trisubstituted by $C_1$-$C_4$-haloalkoxy in the aryl moiety, preferably $C_7$-$C_{10}$-phenylalkyl mono- to trisubstituted by $C_1$-$C_2$-haloalkoxy in the phenyl moiety, particularly preferably $C_7$-$C_{10}$-phenylalkyl mono- to trisubstituted by trifluoromethoxy and trichloromethoxy in the phenyl moiety, such as 4-trifluoromethoxybenzyl and 4-trichloromethoxybenzyl, phenyl substituted by one, two or three phenoxy groups, phenyl di- or trisubstituted by halogen and $C_1$-$C_4$-alkyl, such as 2-methyl-4-chlorophenyl and 3-methyl-4-fluorophenyl, phenyl di- or trisubstituted by halogen and $C_1$-$C_4$-alkoxy, such as 3-chloro-4-methoxyphenyl, phenyl di- or trisubstituted by halogen and $C_1$-$C_4$-haloalkyl, such as 2-chloro-4-trifluoromethylphenyl, phenyl di- or trisubstituted by halogen and phenoxy, such as 3-chloro-4-phenoxyphenyl, phenyl di- or trisubstituted by $C_1$-$C_4$-alkyl and $C_1$-$C_4$-alkoxy, such as 2-methyl-4-methoxyphenyl, phenyl di- or trisubstituted by $c_1$-$C_4$-alkyl and $C_1$-$C_4$-haloalkyl, such as 3-methyl-4-trichloromethylphenyl, phenyl di- or trisubstituted by $C_1$-$C_4$-alkyl and phenoxy, such as 2-methyl-4-phenoxyphenyl, phenyl di- or trisubstituted by $C_1$-$C_4$-alkoxy and $C_1$-$C_4$-haloalkyl, such as 3-trifluoromethyl-4-methoxyphenyl, phenyl di- or trisubstituted by $C_1$-$C_4$-alkoxy and phenoxy, such as 3-methoxy-4-phenoxyphenyl phenyl di- or trisubstituted by $C_1$-$C_4$-haloalkyl and phenoxy, such as 3-trifluoromethyl-4-phenoxyphenyl, phenyl trisubstituted by halogen, $C_1$-$C_4$-alkyl and $C_1$-$C_4$-alkoxy, phenyl trisubstituted by halogen, $C_1$-$C_4$-alkyl and $C_1$-$C_4$-haloalkyl, phenyl trisubstituted by halogen, $C_1$-$C_4$-alkyl and phenoxy, phenyl trisubstituted by halogen, $c_1$-$C_4$-alkoxy and $C_1$-$C_4$-haloalkyl, phenyl trisubstituted by halogen, $C_1$-$C_4$-alkoxy and phenoxy, phenyl trisubstituted by halogen, $C_1$-$C_4$-haloalkyl and phenoxy, phenyl trisubstituted by $C_1$-$C_4$-alkyl, $C_1$-$C_4$-alkoxy and $C_1$-$C_4$-haloalkyl, phenyl trisubstituted by $C_1$-$C_4$-alkyl, $C_1$-$C_4$-alkoxy and phenoxy, phenyl trisubstituted by $C_1$-$C_4$-alkyl, $C_1$-$C_4$-haloalkyl and phenoxy, phenyl trisubstituted by $C_1$-$C_4$-alkoxy, $C_1$-$C_4$-haloalkyl and phenoxy, and $R^3$ and $R^4$ together $(CH_2)_n$ such as $CH_2$, $(CH_2)_2$, $(CH_2)_3$, $(CH_2)_4$, $(CH_2)_5$ and $(CH_2)_6$, preferably $(CH_2)_3$, $(CH_2)_4$, $(CH_2)_5$, $(CH_2)_6$, particularly preferably $(CH_2)_3$ and $(CH_2)_4$, $(CH=CH)_m$, such as $(CH=CH)$, $(CH=CH)_2$, $(CH=CH)_3$, preferably $(CH=CH)_2$, $(CH=CH)_3$ particularly preferably $(CH=CH)_2$, n
from 1 to 6, preferably 3 to 6, particularly preferably 3 and 4, m
from 1 to 3, preferably 2 and 3, particularly preferably 2.

Mono- to trisubstituted means substituted once, twice or three times.

Halogen such as fluorine, chlorine, bromine or iodine, preferably chlorine or bromine.

EXAMPLE 1

1-Methylimidazole 600 ml of 50% strength sodium hydroxide solution, 136 g (2 mol) of imidazole and 16.4 g (0.2 mol) of 1-methylimidazole were introduced into a 1 l four-neck flask with stirrer, thermometer, dropping funnel and reflux condenser, and 312 g (2.2 mol) of methyl iodide were added dropwise with vigorous stirring and cooling in a water bath at 40° C. over the course of 1.5 h. After the addition was complete, the mixture was stirred at 40° C. for 30 min., no exothermic reaction being observed. To work up, the mixture was extracted with chloroform, and the combined organic phases were washed with water and dried over sodium sulfate. The chloroform was then removed and the residue was distilled under reduced pressure. 136.2 g of GC-pure 1-methylimidazole (yield 119.7 g (73%) after subtraction of the product employed as catalyst) of boiling point 72°–73° C. under 13 mbar were obtained.

EXAMPLE 2

1-Ethyl-2-methylimidazole 450 ml of 50% strength sodium hydroxide solution, 123 g (1.5 mol) of 2-methylimidazole and 16.5 g (0.15 mol) of 1-ethyl-2-methylimidazole were introduced into a 1 l four-neck flask with stirrer, thermometer, dropping funnel and reflux condenser, and 257 g (1.65 mol) of ethyl iodide were added dropwise with vigorous stirring at 40° C. After the addition was complete, the mixture was stirred at 40° C. for 30 min, no exothermic reaction being observed. To work up, the mixture was extracted with chloroform, and the combined organic phases were washed with water and dried over sodium sulfate. The chloroform was then removed and the residue was distilled under reduced pressure. 158.5 g of GC-pure 1-ethyl-2-methylimidazole (yield 142 g (86%) after subtraction of the product employed as catalyst) of boiling point 88°–89° C. under 20 mbar were obtained.

EXAMPLE 3

1-Allylimidazole 260 ml of 50% strength sodium hydroxide solution, 102 g (1.5 mol) of imidazole and 16.2 g (0.15 mol) of 1-allylimidazole were introduced into a 1 l four-neck flask with stirrer, thermometer, dropping funnel and reflux condenser, and 126.2 g (1.65 mol) of allyl chloride were added dropwise with vigorous stirring over the course of one hour so that the temperature remained below 40° C. (cooling occasionally with a water bath). After the addition was complete, the mixture was stirred at 40° C. for 30 min. and then diluted with 350 g of water in order to dissolve the salts completely. The organic phase was then separated off, the aqueous phase was extracted with chloroform, and the combined organic phases were dried over sodium sulfate. Removal of the chloroform was followed by distillation under reduced pressure. 165.3 g of GC-pure 1-allylimidazole (yield 149 g (92%) after subtraction of the product employed as catalyst) of boiling point 90°–92° C. under 10 mbar were obtained.

EXAMPLE 4

1-Butylimidazole 260 ml of 50% strength sodium hydroxide solution, 102 g (1.5 mol) of imidazole and 18.6 g (0.15 mol) of 1-butylimidazole were introduced into a 1 l four-neck flask with stirrer, thermometer, dropping funnel and reflux condenser, and 153 g (1.65 mol) of butyl chloride were added dropwise at 50° C. After the addition was complete, the mixture was refluxed for 2 h and then diluted with 350 g of water in order to dissolve the salts completely. The organic phase was then separated off, the aqueous phase was extracted with toluene, and the combined organic phases were dried over sodium sulfate. Removal of the toluene was followed by distillation under reduced pressure. 192 g of GC-pure 1-butylimidazole (yield 173.4 g (93%) after subtraction of the product employed as catalyst) of boiling point 78°-80° C. under 2 mbar were obtained.

EXAMPLE 5

1-Benzylimidazole 260 ml of 50% strength sodium hydroxide solution, 102 g (1.5 mol) of imidazole and 18 g (0.11 mol) of 1-benzimidazole were introduced into a 1 l four-neck flask with stirrer, thermometer, dropping funnel and reflux condenser, and 209 g (1.65 mol) of benzyl chloride were added dropwise at 50° C., cooling with a water bath. After the addition was complete, the mixture was stirred at 50° C. for 30 min. and then diluted with 350 g of water in order to dissolve the salts completely. The organic phase was then separated off, the aqueous phase was extracted with toluene, and the combined organic phases were dried over sodium sulfate. Removal of the toluene was followed by distillation under reduced pressure. 243 g of 99% pure 1-benzylimidazole (yield 222 g (94%) after subtraction of the product employed as catalyst) of boiling point 132°-135° C. under 0.5 mbar were obtained.

EXAMPLE 6

1-Benzyl-2-phenylimidazole 52.5 g (0.415 mol) of benzyl chloride were added dropwise to a vigorously stirred mixture of 54 g (0.375 mol) of 2-phenylimidazole, 6.9 g (0.025 mol) of 1-benzyl-2-phenylimidazole, 300 g of 50% strength sodium hydroxide solution and 100 ml of toluene at 50° C., followed by stirring at 50° C. for 5 h. The mixture was then diluted with water in order to dissolve the precipitated sodium chloride. The organic phase was separated off, and the aqueous phase was extracted once more with toluene. Removal of the toluene was followed by distillation under reduced pressure. 85 g of 99% pure 1-benzyl-2-phenylimidazole (yield 78.3 g (89%) after subtraction of the product employed as catalyst) of boiling point 132°-135° C. under 0.5 mbar were obtained.

EXAMPLE 7

1-Allylimidazole

The reaction was carried out in an entirely similar manner to Example 3, with the difference that 200 g (1.65 mol) of allyl bromide were employed in place of the allyl chloride. The yield was 76%.

Comparative examples similar to Liebigs Ann. Chem. (1983), 1078-1080.

EXAMPLE A

1-Methylimidazole 600 ml of 50% strength sodium hydroxide solution and 136 g (2 mol) of imidazole were introduced into a 1 l four-neck flask with stirrer, thermometer, dropping funnel and reflux condenser, and 312 g (2.2 mol) of methyl iodide were added dropwise with vigorous stirring at 35° C. The mixture was heated to 40° C. and, after a brief period, an exothermic reaction started, during which the temperature rose to 55° C., despite cooling. To work up, the mixture was extracted with chloroform and the combined organic phases were washed with water and dried over sodium sulfate. The chloroform was then removed and the residue was distilled under reduced pressure. 87 g (yield 53%) of GC-pure 1-methylimidazole of boiling point 72°-73° C. under 13 mbar were obtained.

EXAMPLE B

1-Ethyl-2-methylimidazole 450 ml of 50% strength sodium hydroxide solution and 123 g (1.5 mol) of 2-methylimidazole were introduced into a 1 l four-neck flask with stirrer, thermometer, dropping funnel and reflux condenser, and 257 g (1.65 mol) of ethyl iodide were added dropwise with vigorous stirring at 35° C. An exothermic reaction started a few min after addition was complete and, during this, the temperature rose to 55° C. To work up, the mixture was extracted with chloroform and the combined organic phases were washed with water and dried over sodium sulfate. The chloroform was then removed and the residue was distilled under reduced pressure. 68 g (yield 62%; literature report: 73%) of GC-pure 1-ethyl-2-methylimidazole of boiling point 88°-89° C. under 20 mbar were obtained.

EXAMPLE C

1-Allylimidazole 260 ml of 50% strength sodium hydroxide solution and 102 g (1.5 mol) of imidazole were introduced into a 1 l four-neck flask with stirrer, thermometer, dropping funnel and reflux condenser, and 126.2 g (1.65 mol) of allyl chloride were added dropwise with vigorous stirring at 40° C. An exothermic reaction started 30 min after addition was complete and, during this, the temperature rose to 60° C. despite cooling in an ice bath. To work up, the mixture was diluted with 350 g of water in order to dissolve the salts completely. The organic phase was then separated off, and the aqueous phase was extracted with chloroform. After removal of the chloroform from the combined organic phases they were distilled under reduced pressure. 95 g (yeild 58%) of GC-pure 1-allylimidazole of boiling point 90°-92° C. under 10 mbar were obtained.

We claim:

1. In a process for preparing an N-substituted imidazole of the formula

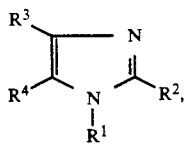 (I)

where
$R^1$ is $C_1$-$C_{20}$-alkyl, $C_2$-$C_{20}$-alkenyl, $C_2$-$C_{20}$-alkynyl, $C_{2-20}$-alkoxyalkyl, $C_3$-$C_{20}$-alkenyloxyalkyl, $C_3$-$C_{12}$-cycloalkyl, $C_4$-$C_{20}$-cycloalkylalkyl, or $C_7$-$C_{20}$-arylalkyl or aryl which is unsubstituted or substituted by $C_1$-$C_8$-alkyl, $C_1$-$C_8$-alkoxy, halogen, $C_1$-$C_4$-haloalkyl, $C_1$-$C_4$-haloalkoxy or phenoxy,
$R^2$, $R^3$ and $R^4$ are each, independently of one another, hydrogen, $C_1$-$C_{20}$-alkyl, $C_2$-$C_{20}$-alkoxyalkyl, $C_3$-$C_{12}$-cycloalkyl, halogen, $C_7$-$C_{20}$-arylalkyl or aryl which is unsubstituted or substituted by $C_1$-$C_8$-alkyl, $C_1$-$C_8$-alkoxy, halogen, $C_1$-$C_4$-haloalkyl, $C_1$-$C_4$-haloalkoxy or phenoxy, or $R^3$ and $R^4$ together form $(CH_2)_n$ or $(CH=CH)_m$ which is unsubstituted or mono- or disubstituted by $C_1$-$C_8$-alkyl, $C_1$-$C_8$-alkoxy and/or halogen and in which n is from 1 to 6 and m is from 1 to 3, by reacting an imidazole of the formula

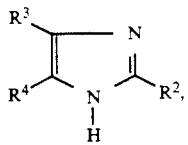 (II)

where
$R^2$, $R^3$ and $R^4$ have the abovementioned meanings, with a halide of the formula

 (III), where X is chlorine, bromine or iodine, and $R^1$ has the abovementioned meanings, in an aqueous hydroxide solution, the improvement which comprises:
carrying out the reaction from the beginning in the presence of from 0.1 to 50 mol % of the N-substituted imidazole I product as a catalyst, based on the imidazole reactant II.

2. A process as claimed in claim 1, wherein the reaction is carried out in the presence of from 1 to 20 mol % of the N-substituted imidazole I product, based on the imidazole reactant II.

3. A process as claimed in claim 1, wherein the reaction is carried out in the presence of from 10 to 70% by weight of an aqueous hydroxide solution.

4. A process as claimed in claim 1, wherein an aqueous alkali metal hydroxide solution is used as the aqueous hydroxide solution.

5. A process as claimed in claim 1, wherein the reaction is carried out at from 0° to 100° C.

6. A process as claimed in claim 1, wherein a chloride or bromide is used as the halide of the formula III.

7. A process as claimed in claim 1 wherein the reaction is carried out at from 15° to 75° C.

8. A process as claimed in claim 1 wherein the reaction is carried out at from 35° to 60° C.

9. A process as claimed in claim 1 wherein the N-substituted imidazole product and the catalyst are identical and each is selected from the group consisting of 1-methylimidazole, 1-ethyl-2-methylimidazole, 1-allylimidazole, 1-butylimidazole, 1-benzylimidazole, and 1-benzyl-2-phenylimidazole.

* * * * *

UNITED STATES PATENT AND TRADEMARK OFFICE
CERTIFICATE OF CORRECTION

PATENT NO. : 5,179,210
DATED : Jan. 12, 1993
INVENTOR(S) : Klaus Ebel

It is certified that error appears in the above-identified patent and that said Letters Patent is hereby corrected as shown below:

On the title page, Item [75] Inventors:
   Change the Inventor's first name from "Kraus" to --Klaus--.

IN THE ABSTRACT:

Line 11, (disregarding the formula I): after "$R^2$," insert --$R^3$--.

Signed and Sealed this

Nineteenth Day of October, 1993

Attest:

BRUCE LEHMAN

*Attesting Officer*   *Commissioner of Patents and Trademarks*